(12) United States Patent
Ueda et al.

(10) Patent No.: US 8,413,513 B2
(45) Date of Patent: Apr. 9, 2013

(54) ULTRASONIC TESTING METHOD AND EQUIPMENT THEREFOR

(75) Inventors: Yoshio Ueda, Osaka (JP); Masaki Yamano, Osaka (JP); Masami Ikeda, Osaka (JP)

(73) Assignee: Nippon Steel & Sumitomo Metal Corporation, Tokyo (JP)

( * ) Notice: Subject to any disclaimer, the term of this patent is extended or adjusted under 35 U.S.C. 154(b) by 0 days.

(21) Appl. No.: 12/934,831

(22) PCT Filed: Mar. 24, 2009

(86) PCT No.: PCT/JP2009/055743
§ 371 (c)(1),
(2), (4) Date: Dec. 13, 2010

(87) PCT Pub. No.: WO2009/119539
PCT Pub. Date: Oct. 1, 2009

(65) Prior Publication Data
US 2011/0113885 A1  May 19, 2011

(30) Foreign Application Priority Data

Mar. 27, 2008 (JP) ................................. 2008-082782

(51) Int. Cl.
*G01N 29/11* (2006.01)
*G01N 29/40* (2006.01)

(52) U.S. Cl.
USPC .......................................................... 73/602

(58) Field of Classification Search ...................... 73/602
See application file for complete search history.

(56) References Cited

U.S. PATENT DOCUMENTS

| 4,322,975 | A | * | 4/1982 | Schmidt et al. | ................. | 73/633 |
| 4,841,489 | A | * | 6/1989 | Ozaki et al. | ....................... | 367/7 |
| 6,128,092 | A | * | 10/2000 | Levesque et al. | ............. | 356/451 |
| 6,622,561 | B2 | * | 9/2003 | Lam et al. | ....................... | 73/622 |
| 2006/0230831 | A1 | * | 10/2006 | Berke | ............................. | 73/602 |
| 2008/0245150 | A1 | * | 10/2008 | Katayama et al. | .............. | 73/602 |
| 2010/0101326 | A1 | * | 4/2010 | Iizuka et al. | .................... | 73/588 |
| 2012/0055252 | A1 | * | 3/2012 | Boehm et al. | ................... | 73/620 |

FOREIGN PATENT DOCUMENTS

| JP | 09-145686 | | 6/1997 |
| JP | 09145686 | A * | 6/1997 |
| JP | 2005-031061 | | 2/2005 |
| WO | 2005/121771 | | 12/2005 |

OTHER PUBLICATIONS

"Ultrasonic Flaw Detection Test III" 2001, Jun. 11, 2001, pp. 57-58 and pp. 117-118.

* cited by examiner

*Primary Examiner* — Peter Macchiarolo
*Assistant Examiner* — Rose M Miller
(74) *Attorney, Agent, or Firm* — Clark & Brody

(57) ABSTRACT

An ultrasonic testing equipment includes a linear array ultrasonic probe in which a plurality of transducers are arranged in a direction orthogonal to the rolling direction of a test object and a signal processing unit. The signal processing unit executes following (1) to (6). (1) Generating an aperture synthetic image of testing signals of each section of the test object. (2) Generating a maximum value distribution of testing signals in the arrangement direction of transducers. (3) Calculating the width of a defect in each section based on the maximum value distribution. (4) Generating a maximum value distribution of the testing signals in the rolling direction based on the maximum value distribution of a plurality of sections of the test object. (5) Calculating the length of the defect based on the maximum value distribution of the testing signals in the rolling direction. (6) Calculating the area of the defect based on the calculated defect length and the calculated defect width of each section.

2 Claims, 8 Drawing Sheets

ULTRASONIC TESTING METHOD AND EQUIPMENT THEREFOR

BACKGROUND OF THE INVENTION

1. Field of the Invention

The present invention relates to an ultrasonic testing method and equipment therefor capable of measuring an area of a defect extending in the rolling direction of a test object with high precision and simply.

2. Description of the Related Art

To guarantee the quality of a rolled metal product (including half-finished products) such as iron and steel products, detection for a defect existing in a product according to an ultrasonic testing and determination on whether or not it is acceptable are carried out. The standard for determining whether or not any product is acceptable is specified by for example, the dimensions of a defect which should be detected. For example, according to API standard 5CT, which is one of Oil Country Tubular Goods (OCTG) related standards, it is stipulated that if any defect which surface is not open within the steel pipe or tube (which is not exposed on the inner and outer surfaces of the steel pipe or tube) is detected, the area of that defect shall not be 260 mm² or more (API Specification 5CT/ISO 11960). The area of the defect is an important factor for guaranteeing the quality of a product.

As a conventional method for calculating the area of any defect quantitatively by ultrasonic testing, there have been known (A) a method for calculating the area of the defect using the height of echo and (B) a method for calculating the area of the defect according to a moving distance in which defect echo appears when an ultrasonic probe is moved, as described in Non-Patent Literature 1 ("Ultrasonic Flaw Detection Test III" 2001, compiled by the Japanese Society for Non-Destructive Inspection, Jun. 11, 2001, pp. 57-58 and pp. 117-118).

Further, (C) a method for calculating the area of the defect using aperture synthetic processing has been proposed in Patent Literature 1 (Japanese Laid-Open Patent Publication No. 2005-31061). Hereinafter, these methods will be described in detail.

(A) Method for Calculating the Area of a Defect Using the Height of Echo

When the size of a defect is smaller than the effective width of ultrasonic beam, the area of the defect can be calculated using a relationship that the area of the defect and the height of echo are proportional to each other.

An echo height $P_R$ from a circular flat defect existing at a point by a distance (distance on the central axis of a circular transducer) $x_1$ from the circular transducer which constitutes the ultrasonic probe is expressed in the following equation (1).

[Equation 1]

$$P_R \approx P_O \cdot \frac{\pi D^2}{4\lambda x_1} \cdot \frac{\pi d^2}{4\lambda x_1} \qquad (1)$$

where, in the above equation (1), $P_O$ means incident sound pressure of ultrasonic wave, $\lambda$ means the wavelength of ultrasonic wave, D means the diameter of a transducer and d means the diameter of a defect.

It is evident from the above equation (1) that the echo height $P_R$ of the defect is proportional to $\pi d^2/4$ which is the area of the defect.

On the other hand, if a test object has a sufficiently wide plane as its bottom surface, the echo height $P_\infty$ of the bottom surface is expressed in the following equation (2) when a distance from the transducer to the bottom surface is $x_2$.

[Equation 2]

$$P_\infty \approx P_O \cdot \frac{\pi D^2}{8\lambda x_2} \qquad (2)$$

The area of the defect can be estimated by obtaining the ratio of the echo height P∞ of the bottom surface and the echo height $P_R$ of the defect according to the above equations (1) and (2) and measuring the distances $x_1$, $x_2$.

However, the above equation (1) is established when the surface of a defect is parallel to the surface of the transducer of the ultrasonic probe. In other words, the calculation method is based on an assumption that the surface of the defect is parallel to the surface of the transducer of the ultrasonic probe and that a maximum echo from the defect is received by the ultrasonic probe. Therefore, if the surface of the defect is tilted with respect to the surface of the transducer, the echo reflected by the defect is hard to receive by the ultrasonic probe thereby reducing its calculation accuracy, which is a problem. Further, the calculation method cannot be employed if the size of the defect is larger than the effective width of ultrasonic beam. Thus, if the test object is a rolled material such as a steel pipe or tube and a steel sheet, it is necessary to use an ultrasonic probe having a large transducer for a planar defect extending in the rolling direction, which is not realistic.

(B) Method for Calculating the Area of a Defect According to a Moving Distance in which Defect Echo Appears by Moving the Ultrasonic Probe In a case where the size of a defect is larger than the effective width of ultrasonic beam, there have been known a method for measuring a range in which the defect echo drops from a maximum echo height to a predetermined level by moving the ultrasonic probe or measuring a range in which the echo height appears over a predetermined height regardless of the maximum echo height, as an indicative length of the defect. According to this method, the length of the defect can be measured with relatively high precision by selecting an ultrasonic probe having smaller transducers than the length of the defect which is a measuring object. As for the planar defect extending in the rolling direction of a rolled material such as a steel pipe or tube and a steel sheet and the like, defect dimensions (defect length) in the rolling direction can be measured with relatively high precision according to the method.

However, it is difficult to satisfy the prerequisite of the method that the size of the defect is larger than the effective width of ultrasonic beam since the dimension of the defect (defect width) in a direction perpendicular to the rolling direction is smaller than that in the rolling direction. The reason is that if the dimension of the transducer is reduced, ultrasonic beam is expanded and if the dimension of the transducer is increased, oscillated ultrasonic beam itself is expanded.

FIG. 1 shows an example of a result of measuring the echo height by moving ultrasonic probes whose the width of transducers are 3.5 mm and 0.7 mm, respectively, with respect to a defect of width 1 mm in its defect width direction at a position apart by 10 mm from the defect (with the ultrasonic probe installed on the surface of a test object in which the defect exists at a position of 10 mm in depth, moving in the defect width direction). As shown in FIG. 1, in a case where any ultrasonic probe is used, the distribution of the echo height in the width direction exhibits a smooth shape originating from a fact that the effective width of the ultrasonic beam is large. If the range in which the echo height drops by 6 dB from the maximum echo height is assumed as a defect width, the defect width to be measured by each ultrasonic probe is 6.3 mm and 2.8 mm, which is larger than an actual defect width (1 mm).

Therefore, In the above method, even if the length of any planar defect extending in the rolling direction, having a small width in a direction perpendicular to the rolling direction of a rolled material such as a steel pipe or tube and a steel sheet can be measured with relatively high precision, the defect width is measured to be larger than its actual width. That is, the above method calculates the area of the defect to be excessive. As a result, any product which is not actually defective is determined to be defective thereby possibly reducing the yield.

(C) Method for Calculating the Area of a Defect by Aperture Synthetic Processing.

On the other hand, Patent Literature 1 has disclosed a method in which three-dimensional imaging data of the interior of a test object is generated based on data collected by executing ultrasonic flaw detection using a group of transducers arranged in a matrix state and then this three-dimensional imaging data is processed to automatically calculate the area of the defect. More specifically, when the area of the defect is automatically calculated from the three-dimensional imaging data, the three-dimensional imaging data is seen through in each axial direction of orthogonal coordinates to project data having a maximum value to a plane. Then, by counting the number of meshes having a higher value than a predetermined threshold on the projection plane, the area of the defect is calculated. This method enables the defect to be displayed at high resolution by employing the aperture synthetic technique when any three-dimensional imaging data is generated. However, there is a problem in calculation efficiency and calculation accuracy when this method is applied to the planar defect or the like of the rolled material. Hereinafter, this method will be described in detail.

It has been known that the resolution of the aperture synthetic-processing image obtained by the aperture synthetic processing depends on an arrangement pitch of the transducer and the size of the aperture. The size of the aperture is similar to the entire dimension of the group of the transducers which receive an echo at the time of the aperture synthetic processing (entire dimension of the group of the transducers arranged in a direction in which the aperture synthetic processing is carried out). Then, it has been known that the smaller the arrangement pitch of the transducers and the larger the size of the aperture (entire dimension of the group of the transducers), the higher the resolution becomes.

Therefore, it can be expected that the dimension of the defect is measured in the aforementioned direction with high precision by using the group of the transducers, the group being configured by arranging a number of the transducers each having a minute dimension in a direction in which the dimension of the defect is required to be measured with high precision. However, the number of the transducers which can be disposed is limited from the perspective of equipment cost, because an electronic circuit relating to exchange and processing of signals is connected to each of these transducers and such an equipment prevalent currently contains about 256 transducers.

As described above, to calculate the area of a defect in a rolled material, it is necessary to measure dimensions of the defect in a direction orthogonal to the rolling direction with high precision because the defect is long in the rolling direction while it is short in the direction orthogonal to the rolling direction, in order to enhance the accuracy of calculation on the area of the defect. When a group of transducers in which the transducers having a minute dimension are arranged densely in a matrix state is used, the resolution in the rolling direction is intensified more than required, while the resolution in the direction orthogonal to the rolling direction is dropped because the size of the aperture is decreased and further, a range which can be measured all at once becomes narrow. For example, to obtain a resolution of about 0.3 mm, at least the arrangement pitch of the transducers needs to be about 0.6 mm, because the arrangement pitch of the transducers needs to be twice or more the resolution in the aperture synthetic processing. When the arrangement pitch of the transducers is 0.6 mm, the size of the aperture is about 0.6× 16=9.6 mm in the case of the group of the transducers in which 16×16 (=256) transducers are arranged in a matrix state. Further, the resolution at a point of a predetermined depth of a test object just below the center of the group of the transducers is assumed to be $\lambda/(2 \sin \theta)$ when the aperture angle is $2\theta$ and the wavelength of ultrasonic wave is $\lambda$. For example, a steel material having a sound velocity of 5960 m/s is employed as a test object and a group of the transducers is placed on the surface of the test object. If the ultrasonic testing frequency is set to 5 MHz, the resolution at a depth of 10 mm from the surface of steel material is about 1.4 mm, indicating that the resolution is dropped. Additionally, a range in which the measurements in the direction orthogonal to the rolling direction can be done all at once is reduced to about 9.6 mm which is similar to the size of an aperture. Therefore, it is difficult to say that the calculation efficiency and calculation accuracy have a balance with each other.

SUMMARY OF THE INVENTION

The present invention has been devised to solve the above problems of the related art and an object of the present invention is to provide an ultrasonic testing method and equipment therefore capable of measuring the area of a defect extending in the rolling direction of a test object with high precision and simply.

As a result of intensive studies for solving the above problems, the inventors of the present invention have considered that the dimension of a defect (defect length) in the rolling direction can be calculated sufficiently according to (B) the method for calculating the area of the defect with the moving distance in which the defect echo appears by moving the ultrasonic probe as with the related art described above. Then, they have considered that the area of the defect can be measured with high precision and simply by combining this method with a method capable of measuring the dimension of the defect (defect width) in a direction orthogonal to the rolling direction with high precision. The inventors have reached an idea that the width of the defect in a certain section can be measured with high precision by disposing a linear array ultrasonic probe in which a plurality of transducers are arranged in line such that the arrangement direction of the transducers agrees with the direction orthogonal to the rolling direction of a test object and performing aperture synthetic processing on testing signals in the section of the test object (section in a direction opposed to the ultrasonic probe) output from the ultrasonic probe. If the arrangement pitch of the transducers of the linear array ultrasonic probe is about 0.6 mm, the size of the aperture is about 153 mm in the linear array ultrasonic probe having 256 transducers, which is a sufficient size for the dimension of the defect. Further, they have reached an idea that the length of the defect can be measured simply based on a distribution in the rolling direction of testing signals when the ultrasonic probe is moved in the rolling direction.

The present invention has been completed based on knowledge of the inventors. That is, the ultrasonic testing method according to the present invention includes the steps of: disposing a linear array ultrasonic probe in which a plurality of transducers are arranged in a direction orthogonal to the rolling direction of a test object such that it is opposed to the test object; moving the ultrasonic probe in the rolling direction of the test object relative to the test object; and calculating the area of a defect existing in the test object based on testing signals output from the ultrasonic probe.

The step of calculating the area of the defect has a feature in including following first to sixth steps.

(1) First step: performing aperture synthetic processing on testing signals output from the ultrasonic probe so as to generate an aperture synthetic image of the testing signals for each section of the test object in the direction opposed to the ultrasonic probe.

(2) Second step: extracting a maximum value of the testing signals in the opposed direction from the aperture synthetic image so as to generate a maximum value distribution of the testing signals in the arrangement direction of transducers.

(3) Third step: calculating both ends in the width direction of the defect in each section of the test object, based on the maximum value distribution of the testing signals in the arrangement direction of the transducers so as to calculate the width of the defect in each section of the test object based on the calculated distance between the both ends.

(4) Fourth step: generating a maximum value distribution of the testing signals in the rolling direction, based on the maximum value distribution of the testing signals in the arrangement direction of the transducers in a plurality of sections of the test object.

(5) Fifth step: calculating the length of the defect based on the maximum value distribution of the testing signals in the rolling direction generated in the fourth step.

(6) Sixth step: calculating the area of the defect based on the length of the defect calculated in the fifth step and the width of the defect in each section calculated in the third step.

According to the present invention, the width of the defect in each section of the test object in the direction opposed to the ultrasonic probe (dimension in the direction orthogonal to the rolling direction) can be measured with high precision by the first step to third step. Then, the length of the defect (dimension in the rolling direction) can be measured simply by the fourth step and the fifth step. Consequently, the area of the defect can be measured with high precision and simply by the sixth step.

In the meantime, the "maximum value of the testing signals" in the present invention means any of a maximum value of the testing signal having a positive polarity and a minimum value of the testing signals having a negative polarity (i.e., maximum value of an absolute value of the ultrasonic signals having a negative polarity).

Further, to solve the above problems, the present invention provides an ultrasonic testing equipment including a linear array ultrasonic probe disposed to be opposed to a test object and movable in the rolling direction of the test object relative to the test object, in which a plurality of transducers are arranged in a direction orthogonal to the rolling direction, and a signal processing unit for calculating the area of a defect existing in the test object based on the testing signals output from the ultrasonic probe, the signal processing unit executing the first step to sixth step.

According to the ultrasonic testing method and equipment of the present invention, the area of the defect extending in the rolling direction of the test object can be measured with high precision and simply.

BRIEF DESCRIPTION OF THE DRAWINGS

FIG. 2A shows a block diagram of the entire configuration and FIG. 2B shows a perspective view for explaining the arrangement of linear array ultrasonic probes;

FIG. 5A shows an example of an aperture synthetic image generated by the aperture synthetic processing portion. FIG. 5B shows an intensity distribution of testing signals along the line A-A in FIG. 5A. FIG. 5C shows a width direction profile generated by the width direction profile arithmetic operating portion of the aperture synthetic image shown in FIG. 5A. FIG. 5D is a diagram for explaining a method for the defect both-ends arithmetic operating portion to calculate both ends of a defect in the width direction based on the width direction profile shown in FIG. 5C.

DETAILED DESCRIPTION OF THE PREFERRED EMBODIMENTS

Hereinafter, an embodiment of an ultrasonic testing method and equipment therefore according to the present invention will be described with reference to the accompanying drawings.

Figure 1:
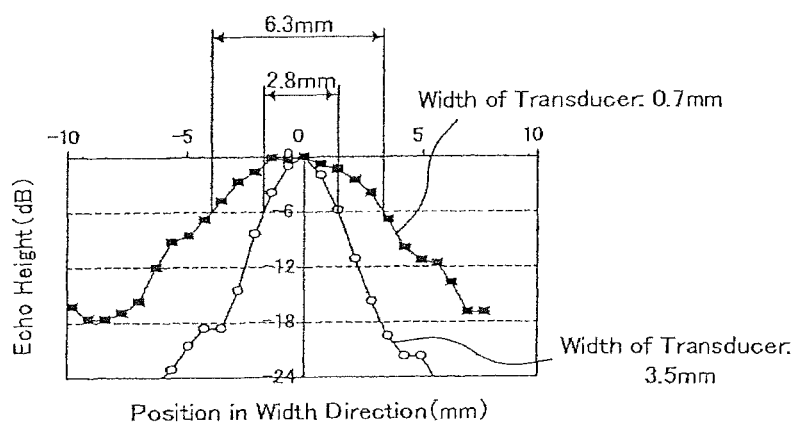
FIG. 1 is an explanatory diagram for explaining a conventional defect area calculating method.
Figures 2A, 2B:
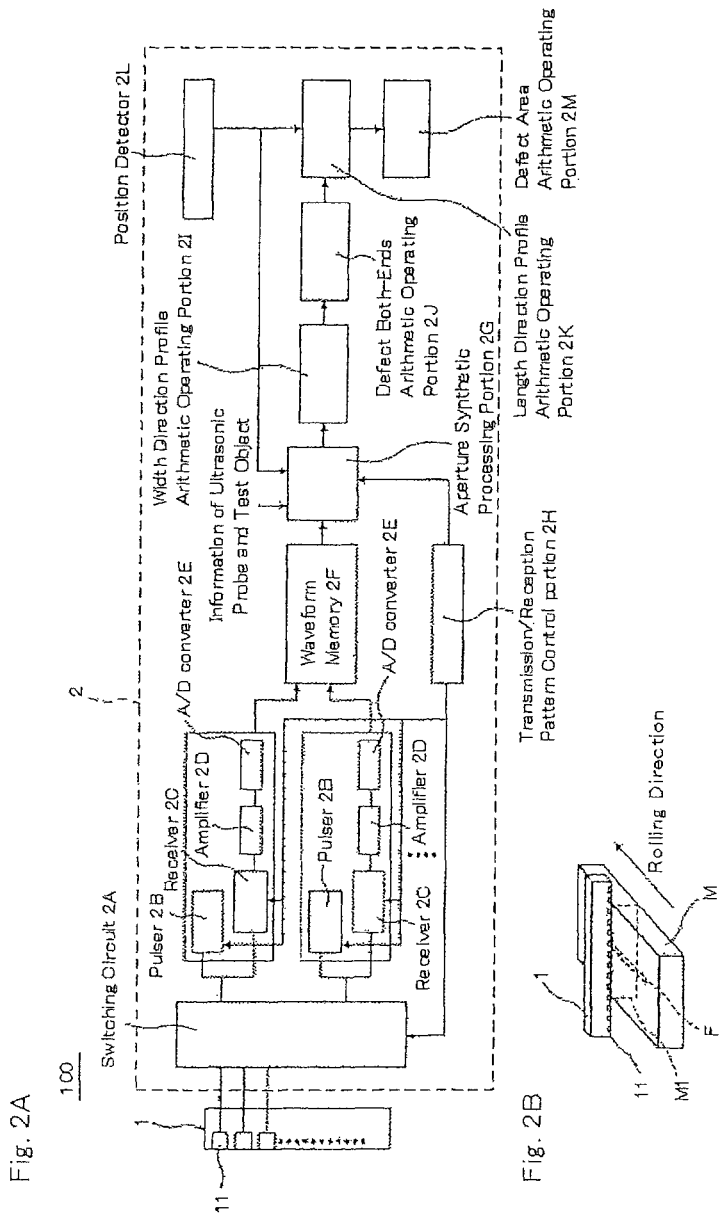
FIGS. 2A and 2B are schematic diagrams each illustrating the schematic configuration of an ultrasonic testing equipment according to an embodiment of the present invention, where

FIGS. 2A and 2B are schematic diagrams each showing the schematic configuration of the ultrasonic testing equipment according to the present embodiment. FIG. 2A shows a block diagram showing the entire configuration and FIG. 2B shows a perspective view for explaining the arrangement of a linear array ultrasonic probe.

As shown in FIGS. 2A and 2B, an ultrasonic testing equipment 100 of the present embodiment includes a linear array ultrasonic probe 1 and a signal processing unit 2 for calculating the area of a defect F existing in a test object M based on testing signals output from the ultrasonic probe 1.

The ultrasonic probe 1 is disposed to be opposed to the test object M and moved in the rolling direction with respect to the test object M, while a plurality of transducers 11 are arranged in a direction orthogonal to the rolling direction.

The signal processing unit 2 includes a switching circuit 2A, a pulser 2B, a receiver 2C, an amplifier 2D, an A/D converter 2E, a waveform memory 2F, an aperture synthetic processing portion 2G, a transmission/reception pattern control portion 2H, a width direction profile arithmetic operating portion 2I, a defect both-ends arithmetic operating portion 2J, a length direction profile arithmetic operating portion 2K, a position detector 2L and a defect area arithmetic operating portion 2M.

The switching circuit 2A is connected to each transducer 11 of the ultrasonic probe 1. The switching circuit 2A selects a transmission transducer 11 and a reception transducer 11 corresponding to a predetermined transmission/reception pattern transmitted from the transmission/reception pattern control portion 2H so as to connect these with the pulsers 2B and the receivers 2C.

The pulser 2B applies a transmission signal to the selected transmission transducer 11. As a result, ultrasonic wave oscillated from the transmission transducer 11 is propagated in the test object M, reflected by the surface of the test object M and a defect F and received by the selected reception transducer 11. The received testing signal is converted to digital data through the receiver 2C, the amplifier 2D and the A/D converter 2E and recorded in the waveform memory 2F.

The aperture synthetic processing portion 2G carries out aperture synthetic processing to testing signals recorded in the waveform memory 2F. At this time, information of the ultrasonic probe 1 and the test object M (for example, a positional relationship between the ultrasonic probe 1 and the test object M, ultrasonic testing frequency of the ultrasonic probe 1, sound velocity in the test object M and coupling medium, the outside diameter of the test object M if it is a pipe or tube, and the like) and the transmission/reception pattern stored in the transmission/reception pattern control portion 2H are used.

Figure 3:
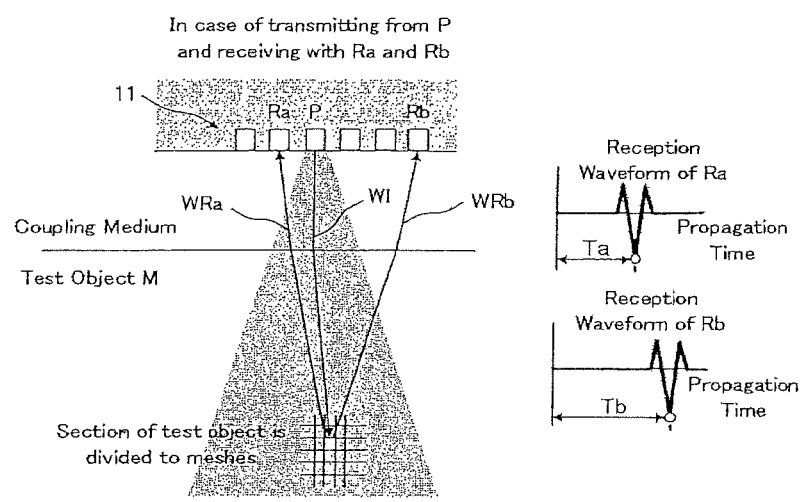
FIG. 3 is an explanatory diagram for explaining aperture synthetic processing to be performed by an aperture synthetic processing portion shown in FIGS. 2A and 2B.

FIG. 3 is an explanatory diagram for explaining the aperture synthetic processing performed by the aperture synthetic processing portion 2G. Upon the aperture synthetic processing, the coordinate space of a section M1 (see FIG. 2B) of the test object M in the direction opposed to the ultrasonic probe 1 is divided to meshes. Then, the value of a testing signal recorded in the waveform memory 2F is obtained and input to each mesh. When determining a value to be obtained, first, the transmission transducer 11 (transducer P in FIG. 3) and the reception transducer 11 (transducers Ra and Rb in FIG. 3) which attracts attention are determined from the transmission transducers 11 and reception transducers 11 selected depending on the transmission/reception pattern. Then, a propagation path WI of ultrasonic wave from the transmission transducer P to the mesh which attracts attention and propagation paths WRa and WRb of ultrasonic wave from the mesh which attracts attention to the reception transducers Ra and Rb are determined. The determination of these propagation paths WI, WRa, and WRb is carried out by selecting an incident point and an outgoing point of the ultrasonic wave so that the propagation paths connecting the transducers P, Ra, and Rb with the incident points or outgoing points of the ultrasonic wave on the test object M and the propagation path connecting the incident point or the outgoing point of the ultrasonic wave on the test object M with the mesh which attracts attention satisfy the Snell's law or Fermat's theorem, based on the positional relationship between the transducers P, Ra, and Rb and the test object M, the sound velocity in the coupling medium and the test object M, and the like. Values of signals corresponding to a propagation time (Ta) of the propagation paths WI and WRa are obtained from testing signals at the reception transducer Ra recorded in the waveform memory 2F and input to the mesh which attracts attention. Then, values of signals corresponding to a propagation time (Tb) of the propagation paths WI and WRb are obtained from the testing signals at the reception transducer Rb recorded in the waveform memory 2F and input to the same mesh which attracts attention (added). The above-described processing is carried out based on combinations of all the transmission transducers 11 and reception transducers 11 selected depending on the transmission/reception pattern so as to determine the value of a testing signal to be input to the mesh which attracts attention. Then, this processing is carried out on all the meshes so as to generate the aperture synthetic image of a section M1. Because the ultrasonic probe 1 is moved in the rolling direction with respect to the test object M, a plurality of the aperture synthetic images are generated for a plurality of section of the test object M. More specifically, the aperture synthetic images are generated for the plurality of sections (for example, sections obtained by a predetermined relative movement) corresponding to relative positions between the ultrasonic probe 1 and the test object M, detected by the position detector 2L.

Figure 4A:
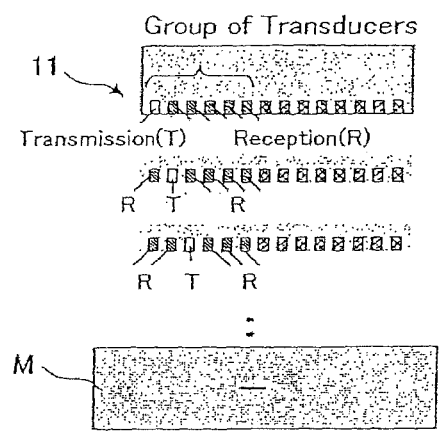
FIGS. 4A and 4B are explanatory diagrams for explaining a transmission/reception pattern of the ultrasonic probe shown in FIGS. 2A and 2B.
Figure 4B:
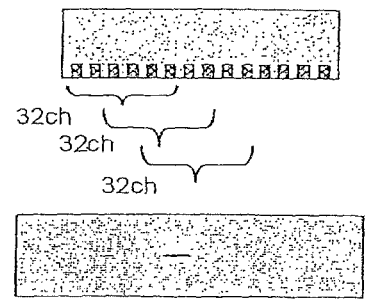

As shown in FIG. 4A, a group of the transducers (part of or all of the transducers 11 which constitute the ultrasonic probe 1) driven as the transmission transducer 11 and the reception transducer 11 is selected and the transmission transducer 11 and the reception transducer 11 are changed over successively in the selected transducer group so as to obtain one aperture synthetic image for the section of one test object M. As shown in FIG. 4B, the same processing is carried out by changing over the transducer group to be selected within the same section so as to obtain a plurality of the aperture synthetic images in the same section (finally, the values of respective meshes of these plurality of aperture synthetic images are summed up so as to obtain one aperture synthetic image).

The width direction profile arithmetic operating portion 2I extracts a maximum value of the testing signals in an opposed direction between the ultrasonic probe 1 and the test object M (depth direction of the test object M) about the aperture synthetic image of each section of the test object M generated by the aperture synthetic processing portion 2G as described above so as to generate a maximum value distribution (hereinafter referred to as a "width direction profile" as required) of the testing signals in the arrangement direction of the transducer 11 (width direction of the defect F).

The defect both-ends arithmetic operating portion 2J calculates both ends in the width direction of the defect F in each section of the test object M based on a width direction profile generated by the width direction profile arithmetic operating portion 2I so as to calculate the width of the defect F in each section of the test object M based on the distance between the calculated both ends.

A processing executed by the width direction profile arithmetic operating portion 2I and the defect both-ends arithmetic operating portion 2J will be described more in detail with reference to FIGS. 5A to 5D.

Figure 5A:
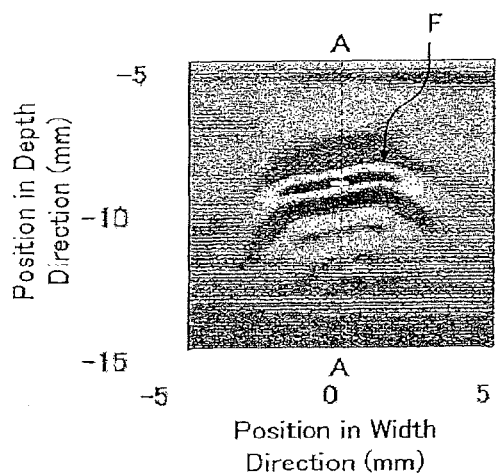
FIGS. 5A to 5D are explanatory diagrams for explaining a processing which the width direction profile arithmetic operating portion and defect both-ends arithmetic operating portion illustrated in FIGS. 2A and 2B perform.
Figure 5B:
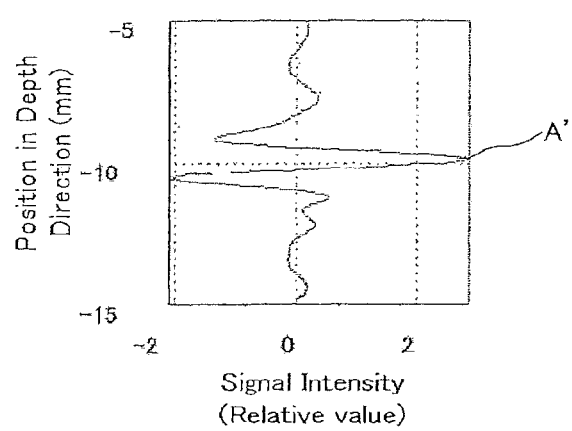
Figure 5C:
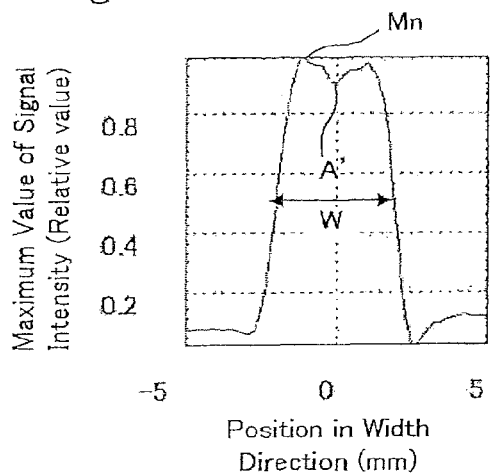
Figure 5D:
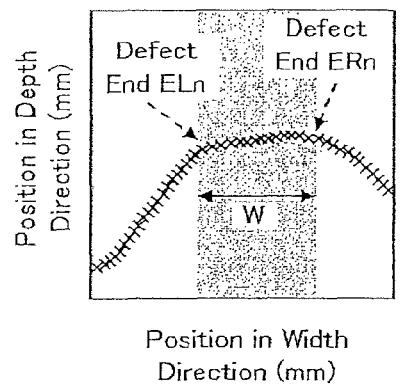

FIGS. 5A to 5D are explanatory diagrams for explaining the processing executed by the width direction profile arithmetic operating portion 2I and the defect both-ends arithmetic operating portion 2J. FIG. 5A shows an example of the aperture synthetic image generated by the aperture synthetic processing portion 2G. FIG. 5B shows an intensity distribution of the testing signals along the line A-A in FIG. 5A. FIG. 5C shows a width direction profile generated by the width direction profile arithmetic operating portion 2I of the aperture synthetic image shown in FIG. 5A. FIG. 5D is a diagram for explaining a method for calculating both ends in the width direction of the defect F by means of the defect both-ends arithmetic operating portion 2J based on the width direction profile shown in FIG. 5C.

The width direction profile arithmetic operating portion 2I reads a value of a testing signal input to a certain mesh located in each width direction (arrangement direction of the transducers 11) position successively about the aperture synthetic image shown in FIG. 5A along a depth direction (in an opposed direction between the ultrasonic probe 1 and the test object M) and extracts its maximum value to plot it at each position in the width direction. For example, as for the width direction position along the line A-A in FIG. 5A, the values of the testing signals input to each mesh are read successively along the line A-A and its maximum value A' is extracted and plotted at a corresponding position in the width direction. At this time, the width direction profile arithmetic operating portion 2I stores coordinates (width direction position, depth direction position) of the mesh in which the extracted maximum value is input.

By repeating the above-described processing for all the positions in the width direction, a width direction profile having a maximum value distribution of the testing signals in the width direction (arrangement direction of the transducers 11) of the defect F is generated as shown in FIG. 5C. The generated width direction profile and the coordinates of the mesh in which the extracted maximum value is input are input to the defect both-ends arithmetic operating portion 2J.

The defect both-ends arithmetic operating portion 2J calculates a range in which the maximum value drops by a predetermined dB from a maximum value Mn of the width direction profile or a range in which the maximum value of the testing signals exceeds a predetermined threshold about the width direction profile (FIG. 5C) generated by the width direction profile arithmetic operating portion 2I. In the example shown in FIG. 5C, a range W in which the maximum value drops by 6 dB from the maximum value Mn is calculated. Then, as shown in FIG. 5D, the defect both-ends arithmetic operating portion 2J reads the coordinates of the mesh in which the maximum value corresponding to both ends of the calculated range W is input so as to adopt them as the coordinates of both ends ELn, ERn of the defect F. Then, the distance between both ends ELn, ERn of the defect is calculated so as to adopt it as the width of defect F.

The width of the defect F in each section of the test object M is calculated by the above-described processing.

Figure 6:
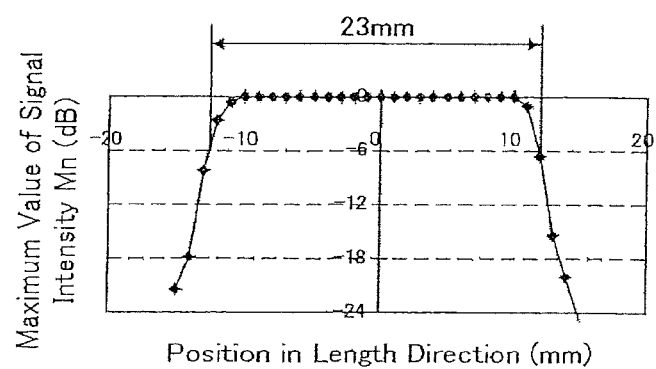
FIG. 6 shows an example of a length direction profile generated by a length direction profile arithmetic operating portion shown in FIGS. 2A and 2B.

The length direction profile arithmetic operating portion 2K generates a maximum value distribution (hereinafter referred to as a "length direction profile" as required) of the testing signals in the rolling direction (length direction of the defect F) from the width direction profile of the plurality of sections of the test object M related with a relative position between the ultrasonic probe 1 detected by the position detector 2L and the object material M. More specifically, the maximum values Mn (see FIG. 5C) of the width direction profile in each section are plotted at positions in the length direction (rolling direction) of a rolling object material M correlated with each section to generate the length direction profile as shown in FIG. 6.

Then, the length direction profile arithmetic operating portion 2K calculates a length of the defect F based on the length direction profile. More specifically, a range in which the maximum value drops by only the predetermined dB from the maximum value of the length direction profile or a range in which the maximum value Mn of the testing signal exceeds the predetermined threshold is calculated as the length of the defect F.

Figure 7:
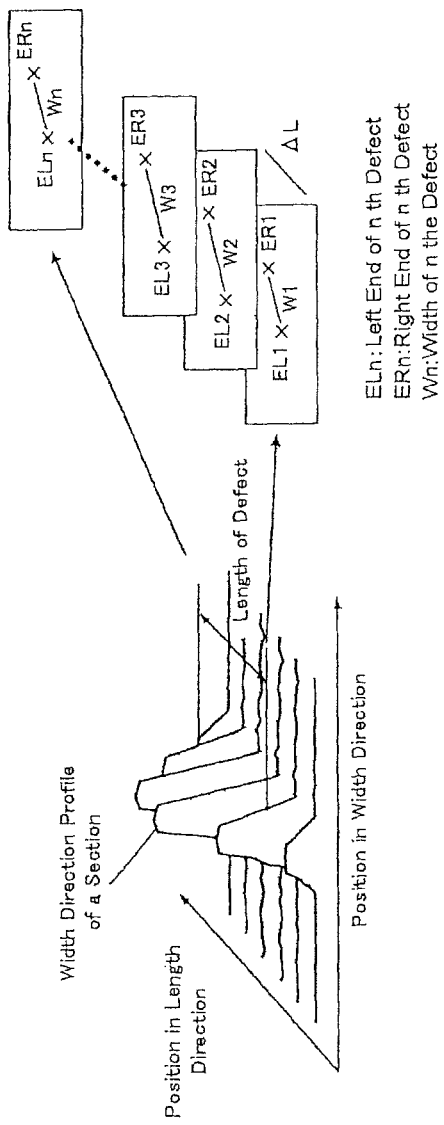
FIG. 7 is an explanatory diagram for explaining a processing which the defect area arithmetic operating portion shown in FIGS. 2A and 2B performs.

The defect area arithmetic operating portion 2M calculates the area of the defect F based on the length of the defect F calculated by the length direction profile arithmetic operating portion 2K and the width of the defect F in each section calculated by the defect both-ends arithmetic operating portion 2J. More specifically, as shown in FIG. 7, a sum of products of the width Wn of the defect F calculated about a section within a range corresponding to the length of the defect F and a distance $\Delta L$ in the rolling direction (length direction of the defect F) between the sections is calculated within a range corresponding to the length of the defect F so as to calculate the area of the defect F.

According to the ultrasonic testing method using the ultrasonic testing equipment 100 of this embodiment, the area of the defect F extending in the rolling direction of the test object M can be measured with high precision and simply.

Examples

Hereinafter, the present invention will be described more in detail by indicating examples.

The ultrasonic test was carried out by an ultrasonic testing equipment of the present invention whose schematic configuration was shown in FIGS. 2A and 2B in order to find a defect in a flat bottom groove (tilted by 10° with respect to the horizontal direction of the flat panel, 3.6 mm in width and 20 mm in length) in the flat panel. A linear array ultrasonic probe having an ultrasonic testing frequency of 5 MHz, a transducer arrangement pitch of 0.5 mm, and 64 transducers, and in which the length of the transducer in a direction orthogonal to the arrangement direction was 6 mm was used. The aperture synthetic image was generated each time when the ultrasonic probe and a test object were moved by 1 mm relative to each other.

FIG. 5A shows an example of the aperture synthetic image obtained by this embodiment. To obtain the aperture synthetic image, ultrasonic wave was sent by any one of transducers and received by the 64 transducers and then, the transmission transducer was changed over successively from a first transducer up to $64^{th}$ transducer. A width direction profile shown in FIG. 5C was generated for this aperture synthetic image, both ends in the width direction of the defect was calculated as shown in FIG. 5D and then, the width of the defect in each section of the flat panel was calculated according to the calculated distance between the both ends. The defect width calculated about the aperture synthetic image in FIG. 5A was 3.2 mm. This value was calculated with high precision although it was calculated to be slightly smaller than an actual defect width of 3.6 mm.

FIG. 6 shows a length direction profile obtained by this embodiment. A range in which the defect width drops by 6 dB from the maximum value of the length direction profile was calculated as the length of the defect. The calculated defect length was 23 mm and although it was slightly larger than the actual defect length of 20 mm, it can be said that the defect length could be calculated with high precision.

The sum of products of the defect width calculated about a section within a range corresponding to the defect length and a distance (1 mm) in the rolling direction (direction of the defect length) between the respective sections is calculated within the range corresponding to the defect length so as to calculate the area of the defect. The calculated area of the defect was 81 mm$^2$ and it is made evident that the defect can be measured with an error of about +13% the actual defect area of 72 mm$^2$.

Figure 8:
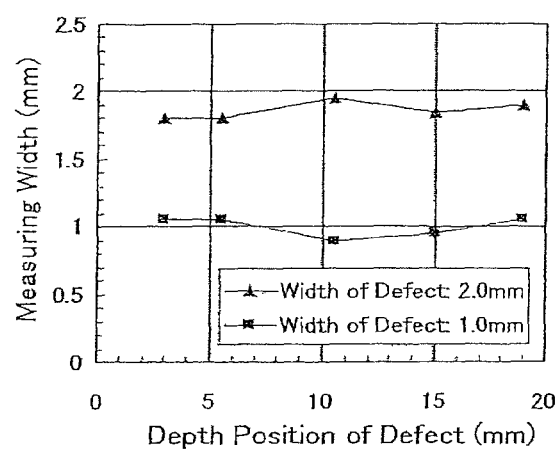
FIG. 8 shows an example of a result of calculation of defect widths according to the embodiment of the present invention.

FIG. 8 shows a result of calculation of the widths of flat bottom holes 2.0 mm and 1.0 mm in width, each having a different depth in the flat panel, using the ultrasonic testing equipment of this embodiment. As shown in FIG. 8, it is evident that the width of the defect can be calculated with high precision regardless of a depth position of the defect (flat bottom hole).

The area of the flat bottom groove (tilted by 10° with respect to the horizontal direction of the flat panel, 3.6 mm in width and 20 mm in length) in the flat panel was calculated as a defect using the ultrasonic testing equipment of this embodiment. Further, the area of the same defect was calculated as a comparative example using an ordinary ultrasonic probe. More specifically, the ultrasonic probe was moved in the length direction and width direction of the defect and the length and width of the defect were calculated according to a moving distance in which a defect echo appears. Consequently, the area of the defect was calculated (which is similar to the above-described related art (B)). Table 1 shows its result.

TABLE 1

| Defect area measuring method | Specification of ultrasonic probe | Defect actual area | Result of area measurement | Error |
|---|---|---|---|---|
| Present invention (width direction aperture synthetic + length direction scanning) | Ultrasonic testing frequency: 5 MHz Arrangement pitch: 0.5 mm Number of transducers: 64 ch Length: 6 mm | 36 mm$^2$ Width: 1.8 mm Length: 20 mm | 41 mm$^2$ | +13.9% |
| Comparative example (width direction scanning + length direction scanning) | Ultrasonic testing frequency: 5 MHz Transducer diameter: 6.35 mm | | 62 mm$^2$ | +72.2% |

As indicated in Table 1, according to the present invention, it is evident that the area of the defect can be calculated with higher precision than the related art.

What is claimed is:

1. An ultrasonic testing method comprising the steps of:
disposing a linear array ultrasonic probe in which a plurality of transducers are arranged in a direction orthogonal to the rolling direction of a test object such that it is opposed to the test object;
moving the ultrasonic probe in the rolling direction of the test object relative to the test object; and
calculating the area of a defect existing in the test object by a signal processing unit based on testing signals output from the ultrasonic probe, wherein
the step of calculating the area of the defect by the signal processing unit includes:
a first step of performing aperture synthetic processing on testing signals output from the ultrasonic probe so as to generate an aperture synthetic image of the testing signals about each section of the test object in the direction opposed to the ultrasonic probe;
a second step of extracting a maximum value of the testing signals in the opposed direction from the aperture synthetic image so as to generate a maximum value distribution of the testing signals in the arrangement direction of the transducers;
a third step of calculating both ends in the width direction of the defect in each section of the test object, based on the maximum value distribution of the testing signals in the arrangement direction of the transducers so as to calculate the width of the defect in each section of the test object based on the calculated distance between the both ends;
a fourth step of generating a maximum value distribution of the testing signals in the rolling direction, based on the maximum value distribution of the testing signals in the arrangement direction of the transducers in a plurality of sections of the test object;
a fifth step of calculating the length of the defect based on the maximum value distribution of the testing signals in the rolling direction generated in the fourth step; and
a sixth step of calculating the area of the defect based on the length of the defect calculated in the fifth step and the width of the defect in each section calculated in the third step.

2. An ultrasonic testing equipment comprising:
a linear array ultrasonic probe disposed to be opposed to a test object and movable in the rolling direction of the test object relative to the test object, in which a plurality of transducers are arranged in a direction orthogonal to the rolling direction; and
a signal processing unit for calculating the area of a defect existing in the test object based on testing signals output from the ultrasonic probe, wherein
the signal processing unit comprises:
an aperture synthetic processing portion for performing aperture synthetic processing on testing signals output from the ultrasonic probe so as to generate an aperture synthetic image of the testing signals about each section of the test object in the direction opposed to the ultrasonic probe;
a width direction profile arithmetic operating portion for extracting a maximum value of the testing signals in the opposed direction from the aperture synthetic image so as to generate a maximum value distribution of the testing signals in the arrangement direction of the transducers;
a defect both-ends arithmetic operating portion for calculating both ends in the width direction of the defect in each section of the test object, based on the maximum value distribution of the testing signals in the arrangement direction of the transducers so as to calculate the width of the defect in each section of the test object based on the calculated distance between the both ends;
a length direction profile arithmetic operating portion for generating a maximum value distribution of the testing signals in the rolling direction, based on the maximum value distribution of the testing signals in the arrangement direction of the transducers in plurality of sections of the test object and for calculating the length of the defect based on the generated maximum value distribution of the testing signals in the rolling direction; and
a defect area arithmetic operating portion for calculating the area of the defect based on the length of the defect calculated by the length direction profile arithmetic operating portion and the width of the defect in each section calculated by the defect both-ends arithmetic operating portion.

* * * * *